United States Patent
Okajima et al.

(10) Patent No.: US 7,982,213 B2
(45) Date of Patent: Jul. 19, 2011

(54) PHENANTHROLINE COMPOUND AND ORGANIC LIGHT EMITTING DEVICE USING SAME

(75) Inventors: Maki Okajima, Tokyo (JP); Tatsundo Kawai, Hadano (JP); Takao Takiguchi, Tokyo (JP); Koichi Suzuki, Yokohama (JP); Akihiro Senoo, Kawasaki (JP); Toshinori Hasegawa, Yokohama (JP); Keiji Okinaka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 296 days.

(21) Appl. No.: 12/436,507

(22) Filed: May 6, 2009

(65) Prior Publication Data
US 2009/0218940 A1    Sep. 3, 2009

Related U.S. Application Data

(62) Division of application No. 10/527,192, filed as application No. PCT/JP2003/011485 on Sep. 9, 2003, now Pat. No. 7,550,594.

(30) Foreign Application Priority Data

Sep. 19, 2002   (JP) ................................. 2002-272408

(51) Int. Cl.
H01L 33/02    (2010.01)
C07D 471/02   (2006.01)

(52) U.S. Cl. .................... 257/40; 257/E51.038; 546/81

(58) Field of Classification Search .................... 257/40, 257/E51.038; 546/81
See application file for complete search history.

(56) References Cited

U.S. PATENT DOCUMENTS

| | | | |
|---|---|---|---|
| 4,539,507 A | 9/1985 | VanSlyke et al. | 313/504 |
| 4,720,432 A | 1/1988 | VanSlyke et al. | 428/457 |
| 4,885,211 A | 12/1989 | Tang et al. | 428/457 |
| 5,130,603 A | 7/1992 | Tokailin et al. | 313/504 |
| 5,151,629 A | 9/1992 | VanSlyke et al. | 313/504 |
| 5,227,252 A | 7/1993 | Murayama et al. | 428/690 |
| 5,247,190 A | 9/1993 | Friend et al. | 277/40 |
| 5,317,169 A | 5/1994 | Nakano et al. | 257/40 |
| 5,382,477 A | 1/1995 | Saito et al. | 428/690 |
| 5,393,614 A | 2/1995 | Nakada | 428/690 |
| 5,409,783 A | 4/1995 | Tang et al. | 428/690 |
| 5,514,878 A | 5/1996 | Holmes et al. | 257/40 |
| 5,672,678 A | 9/1997 | Holmes et al. | 528/373 |
| 5,726,457 A | 3/1998 | Nakano et al. | 257/40 |
| 6,010,796 A | 1/2000 | Kijima | 428/690 |
| 6,093,864 A | 7/2000 | Tokailin et al. | 585/25 |
| 6,524,728 B1 | 2/2003 | Kijima et al. | 428/690 |
| 6,929,873 B2 | 8/2005 | Tsuboyama et al. | 428/690 |
| 6,972,334 B1 | 12/2005 | Shibanuma et al. | 546/88 |

FOREIGN PATENT DOCUMENTS

| | | |
|---|---|---|
| EP | 1 097 981 | 5/2001 |
| EP | 1 098 980 | 5/2001 |
| JP | 05-202356 | 8/1993 |
| JP | 05-247460 | 9/1993 |
| JP | 07-82551 | 3/1995 |
| JP | 09-202878 | 8/1997 |
| JP | 09-227576 | 9/1997 |
| JP | 2001-131174 | 5/2001 |
| JP | 2001-135482 | 5/2001 |
| JP | 2001-267080 | 9/2001 |
| JP | 2002-50481 | 2/2002 |

OTHER PUBLICATIONS

Case, "Substituted 1,10Phenanthrolines, IV, Bromo Derivatives", J. Org. Chem. 16, pp. 941-945 (1951).
Tang et al., "Organic electroluminescent diodes", Appl. Phys. Lett. 51, (12) 913-915 (Sep. 1987).
Burroughs et al., "Light-emitting diodes based on conjugated polymers", Nature, 347, 539-541 (Oct. 1990).
Tzalis, et al., "Simple One-Step Synthesis . . . of Metal Chelates", Tetrahedron Letters, 36, 20, 3489-3490 (1995).
Miyaura et al., "Palladium-Catalyzed Cross-Coupling Reactions of Organoboron Compounds", Chem. Rev. 95, 2457-2483 (1995).
Baldo et al., "Highly efficient phosphorescent . . . devices", Nature, 395, 151-154 (Sep. 1998).
Ito et al., "Syntheses of Phenanthroline . . . Devices"; Polymer Reprints Japan, vol. 51, No. 11 (2002), The Society of Polymer Science, Japan.
Shibanuman, et al. Caplus English Abstract EP 1097980, May 2001.
F.A. Dorwald, "Side Reactions in Organic Synthesis", Wiley: Weinheim, p. IX of Preface, 2005.

Primary Examiner — Robert Havlin
(74) Attorney, Agent, or Firm — Fitzpatrick, Cella, Harper & Scinto

(57) ABSTRACT

A novel phenanthroline compound is provided which is represented by the general formula [I]:

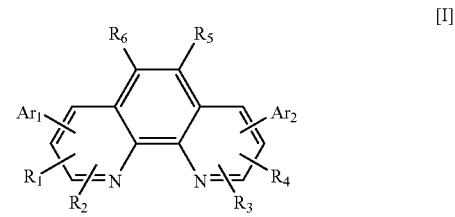

(wherein $R_1$, $R_2$, $R_3$, $R_4$, $R_5$ and $R_6$ are the same or different and each is selected from a hydrogen atom, an unsubstituted or substituted alkyl group, an unsubstituted or substituted aralkyl group, an unsubstituted or substituted aryl group, an unsubstituted or substituted heterocyclic group, and a halogen atom; and $Ar_1$ and $Ar_2$ are the same or different and each is selected from an unsubstituted or substituted fluorenyl group, an unsubstituted or substituted fluoranthenyl group, an unsubstituted or substituted perylenyl group, and an unsubstituted or substituted carbazolyl group). An organic light emitting device using the phenanthroline compound is also provided that has a light output with a high efficiency and a high luminance and has a high long-term durability.

7 Claims, 3 Drawing Sheets

PHENANTHROLINE COMPOUND AND ORGANIC LIGHT EMITTING DEVICE USING SAME

CROSS-REFERENCE TO RELATED APPLICATIONS

This application is a divisional application of U.S. application Ser. No. 10/527,192, filed Mar. 10, 2005, which is a national stage under 35 U.S.C. §371 of PCT/JP03/11485, filed Sep. 9, 2003. This application claims priority of Japanese Patent Application No. 2002-272408, filed on Sep. 19, 2002 under 35 U.S.C. §119. The contents of all of the aforementioned applications are hereby incorporated by reference herein in their entireties.

TECHNICAL FIELD

The present invention relates to a novel organic compound and an organic light emitting device using the same.

BACKGROUND ART

An organic light emitting device is a device in which a thin film containing a fluorescent organic compound or a phosphorescent organic compound is interposed between an anode and a cathode; excitons of the fluorescent compound or the phosphorescent compound are generated by injection of electrons and holes from the electrodes and a light radiated when the excitons return to the ground state is utilized.

In a research by Eastman Kodak Company in 1987 (non-patent document 1), there is reported a light emission of about 1,000 cd/m$^2$ at an applied voltage of about 10 V for a device of functionally separated two-layer structure using ITO for an anode and a magnesium/silver alloy for a cathode, respectively, an aluminium-quinolinol complex as an electron-transporting material and a light emitting material and a triphenylamine derivative as a hole transporting material. Related patents include patent documents 1 to 3.

In addition, light emission of from ultraviolet region to infrared region is possible by changing the type of the fluorescent organic compound and researches of various compounds have been conducted actively recently. For example, they are described in patent documents 4 to 11.

In recent years, there have been a number of studies in which phosphorescent compounds are used as a light emitting material and an energy in a triplet state is used for an EL (electro luminescent) emission. A group of Princeton University has reported that an organic light emitting device using an iridium complex as a light emitting material exhibits a high light emission efficiency (non-patent document 2).

Moreover, a group of Cambridge University has reported (non-patent document 3) an organic light emitting device using a conjugated polymer other than the organic light emitting device using the low-molecular materials as described above. In this report light emission in a monolayer is confirmed by forming a film of polyphenylenevinylene (PPV) in a coating system.

Related patents on organic light emitting devices using conjugated polymers include patent documents 12 to 16.

Thus, recent progress in organic light emitting devices is remarkable, and possibilities for a wide range of applications are indicated since it is characterized in that a thin and light-weight light emitting device having a high luminance at a low applied-voltage, diversity of light emitting wavelength and high-speed response can be prepared.

However, a higher-luminance light output or high conversion efficiency is required under present circumstances. In addition, there are numbers of problems in terms of durability such as variation with the elapse of time during use for a long period of time and the deterioration due to an atmospheric gas including oxygen or humidity. Moreover, the light emission of blue, green and red having a good color purity is required for applications such as a full-color display, but these issues are not sufficiently satisfied.

On the other hand, phenanthroline compounds are used as an electron transporting material or a light emitting material by the excellent electron transporting property thereof. Examples of documents in which the phenanthroline compounds are reported to be used for an organic light emitting device include patent references 17 to 21, but their properties when they are used as a light emitting material or an electron transporting material are not sufficient.

[Patent Document 1]
U.S. Pat. No. 4,539,507
[Patent Document 2]
U.S. Pat. No. 4,720,432
[Patent Document 3]
U.S. Pat. No. 4,885,211
[Patent Document 4]
U.S. Pat. No. 5,151,629
[Patent Document 5]
U.S. Pat. No. 5,409,783
[Patent Document 6]
U.S. Pat. No. 5,382,477
[Patent Document 7]
U.S. Pat. No. 5,130,603; U.S. Pat. No. 6,093,864
[Patent Document 8]
U.S. Pat. No. 5,227,252
[Patent Document 9]
Japanese Patent Application Laid-Open No. H5-202356 (no corresponding foreign document)
[Patent Document 10]
Japanese Patent Application Laid-Open No. H9-202878 (no corresponding foreign document)
[Patent Document 11]
Japanese Patent Application Laid-Open No. H9-227576 (no corresponding foreign document)
[Patent Document 12]
U.S. Pat. No. 5,247,190
[Patent Document 13]
U.S. Pat. No. 5,514,878
[Patent Document 14]
U.S. Pat. No. 5,672,678
[Patent Document 15]
U.S. Pat. No. 5,317,169; U.S. Pat. No. 5,726,457
[Patent Document 16]
Japanese Patent Application Laid-Open No. H5-247460 (no corresponding foreign document)
[Patent Document 17]
U.S. Pat. No. 5,393,614
[Patent Document 18]
Japanese Patent Application Laid-Open No. H7-82551 (no corresponding foreign document)
[Patent Document 19]
U.S. Pat. No. 6,010,796
[Patent Document 20]
Japanese Patent Application Laid-Open No. 2001-267080 (no corresponding foreign document)
[Patent Document 21]
Japanese Patent Application Laid-Open No. 2001-131174 (no corresponding foreign document)

[Non-Patent Document 1]
  Appl. Phys. Lett. 51, 913 (1987)
[Non-Patent Document 2]
  Nature, 395, 151 (1998)
[Non-Patent Document 3]
  Nature, 347, 539 (1990)

DISCLOSURE OF THE INVENTION

It is, therefore, an object of the present invention to provide a novel phenanthroline compound.

It is another object of the present invention to provide an organic light emitting device having a light output with an extremely high efficiency and a high luminance using a specific phenanthroline compound.

It is still another object of the present invention to provide an extremely durable organic light emitting device.

It is yet another object of the present invention to provide an organic light emitting device that is easily produced and can be prepared at a relatively low cost.

Specifically, the present invention provides a phenanthroline compound represented by any one of the following general formulas [I] to [III]:

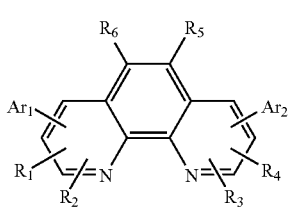

[I]

(wherein $R_1$, $R_2$, $R_3$, $R_4$, $R_5$ and $R_6$ are the same or different and each is selected from a hydrogen atom, an unsubstituted or substituted alkyl group, an unsubstituted or substituted aralkyl group, an unsubstituted or substituted aryl group, an unsubstituted or substituted heterocyclic group, and a halogen atom; and $Ar_1$ and $Ar_2$ are the same or different and each is selected from an unsubstituted or substituted fluorenyl group, an unsubstituted or substituted fluoranthenyl group, an unsubstituted or substituted perylenyl group, and an unsubstituted or substituted carbazolyl group);

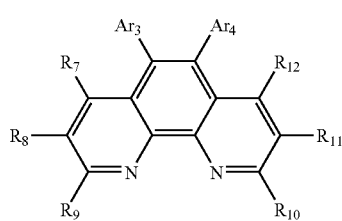

[II]

(wherein $R_7$, $R_8$, $R_9$, $R_{10}$, $R_{11}$ and $R_{12}$ are the same or different and each is selected from a hydrogen atom, an unsubstituted or substituted alkyl group, an unsubstituted or substituted aralkyl group, an unsubstituted or substituted aryl group, an unsubstituted or substituted heterocyclic group, and a halogen atom; and $Ar_3$ and $Ar_4$ are the same or different and each is selected from an unsubstituted or substituted fluorenyl group, an unsubstituted or substituted fluoranthenyl group, an unsubstituted or substituted perylenyl group, and an unsubstituted or substituted carbazolyl group); and

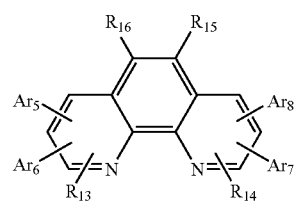

[III]

(wherein $R_{13}$, $R_{14}$, $R_{15}$ and $R_{16}$ are the same or different and each is selected from a hydrogen atom, an unsubstituted or substituted alkyl group, an unsubstituted or substituted aralkyl group, an unsubstituted or substituted aryl group, an unsubstituted or substituted heterocyclic group, and a halogen atom; and $Ar_5$, $Ar_6$, $Ar_7$ and $Ar_8$ are the same or different and each is selected from an unsubstituted or substituted fluorenyl group, an unsubstituted or substituted fluoranthenyl group, an unsubstituted or substituted perylenyl group, and an unsubstituted or substituted carbazolyl group).

In the phenanthroline compounds of the present invention, the fluorenyl group is preferably represented by the following general formula [IV]:

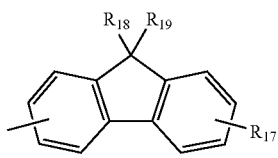

[IV]

(wherein $R_{17}$ is selected from a hydrogen atom, an unsubstituted or substituted alkyl group, an unsubstituted or substituted aralkyl group, an unsubstituted or substituted aryl group, an unsubstituted or substituted heterocyclic group, a substituted amino group, a cyano group, and a halogen atom; and $R_{18}$ and $R_{19}$ are the same or different and each is selected from a hydrogen atom, an unsubstituted or substituted alkyl group, an unsubstituted or substituted aralkyl group, an unsubstituted or substituted aryl group, and an unsubstituted or substituted heterocyclic group).

Also, the fluoranthenyl group is preferably represented by the following general formula [V]:

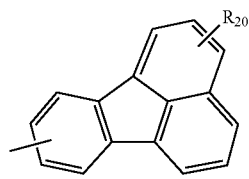

[V]

(wherein $R_{20}$ is selected from a hydrogen atom, an unsubstituted or substituted alkyl group, an unsubstituted or substituted aralkyl group, an unsubstituted or substituted aryl group, an unsubstituted or substituted heterocyclic group, a substituted amino group, a cyano group, and a halogen atom).

Also, the perylenyl group is preferably represented by the following general formula [VI]:

[VI]

(wherein $R_{21}$ is selected from a hydrogen atom, an unsubstituted or substituted alkyl group, an unsubstituted or substituted aralkyl group, an unsubstituted or substituted aryl group, an unsubstituted or substituted heterocyclic group, a substituted amino group, a cyano group, and a halogen atom).

Also, the carbazolyl group is preferably represented by the following general formula [VII]:

[VII]

(wherein $R_{22}$ and $R_{23}$ are the same or different and each is selected from a hydrogen atom, an unsubstituted or substituted alkyl group, an unsubstituted or substituted aralkyl group, an unsubstituted or substituted aryl group, an unsubstituted or substituted heterocyclic group, a substituted amino group, a cyano group, and a halogen atom).

Further, the present invention provides an organic light emitting device comprising a pair of electrodes consisting of an anode and a cathode, and a layer comprising an organic compound comprising at least one of the above-mentioned phenanthroline compounds, interposed between the pair of electrodes.

BEST MODE FOR CARRYING OUT THE INVENTION

Figure 1:
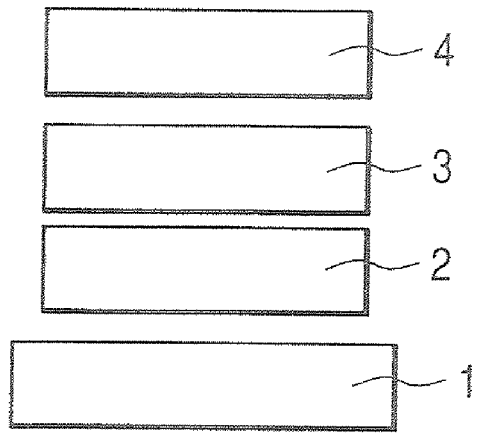
FIG. 1 is a sectional view illustrating an example of the organic light emitting device according to the present invention.

The present invention will now be described in detail.

The phenanthroline compounds of the present invention will be first described.

Preferably, the phenanthroline compounds of the present invention are represented by the above general formulas [I] to [III], wherein a fluorenyl group is represented by the above general formula [IV], a fluoranthenyl group by the above general formula [V], a perylenyl group by the above general formula [VI] and a carbazolyl group by the above general formula [VII].

Specific examples for the substituent groups in the above general formulas [I]-[VII] are shown below.

The alkyl group includes methyl, ethyl, n-propyl, iso-propyl, n-butyl, ter-butyl, octyl or the like.

The aralkyl group includes benzyl, phenethyl or the like.

The aryl group includes phenyl, biphenyl, terphenyl or the like.

The heterocyclic group includes thienyl, pyrolyl, pyridyl, oxazolyl, oxadiazolyl, thiazolyl, thidiazolyl, terthienyl or the like.

The substituted amino group includes dimethylamino, diethylamino, dibenzylamino, diphenylamino, ditolylamino, dianisolylamino or the like.

The halogen atom includes fluorine, chlorine, bromine, iodine or the like.

The substituent groups that the above substituent groups may have include alkyl groups such as methyl, ethyl and propyl; aralkyl groups such as benzyl and phenethyl; aryl groups such as phenyl and biphenyl; heterocyclic groups such as thienyl, pyrolyl and pyridyl; amino groups such as dimethylamino, diethylamino, dibenzylamino, diphenylamino, ditolylamino and dianisolylamino; alkoxyl groups such as methoxyl, ethoxyl, propoxyl and phenoxyl; cyano group; and halogen atoms such as fluorine, chlorine, bromine and iodine.

The followings are typical examples of the phenanthroline compounds of the present invention, but the present invention is not limited thereto:

[I]

Typical Examples of Compounds of Formula [I]

Exemplary Compound Nos. 1-16

1

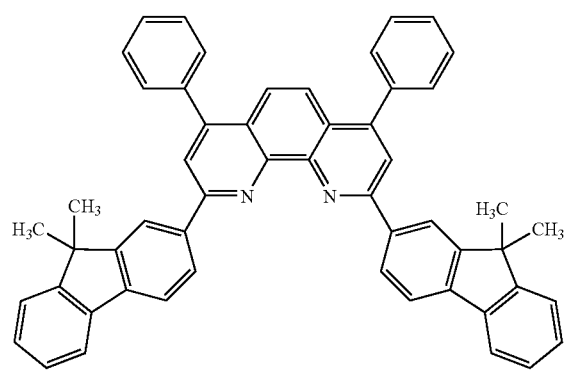
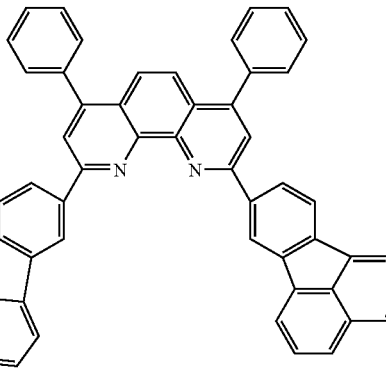
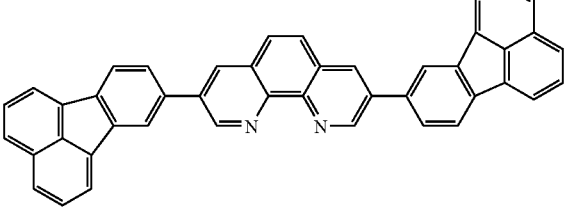
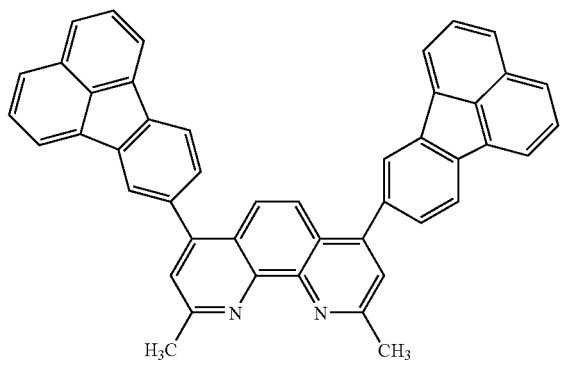
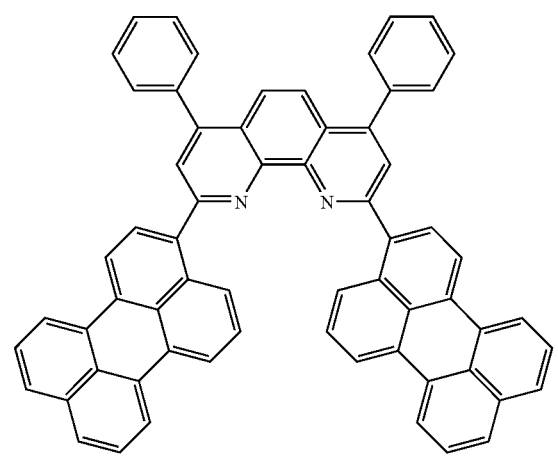

11
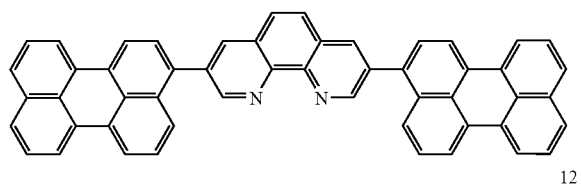
12
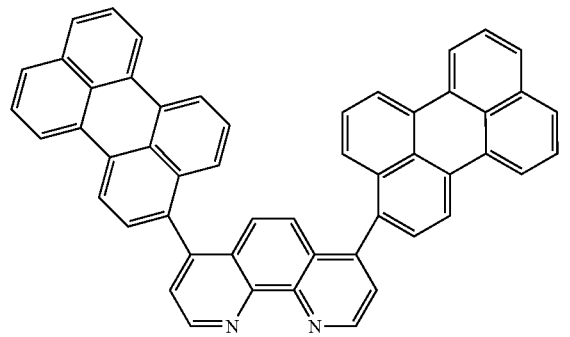
13
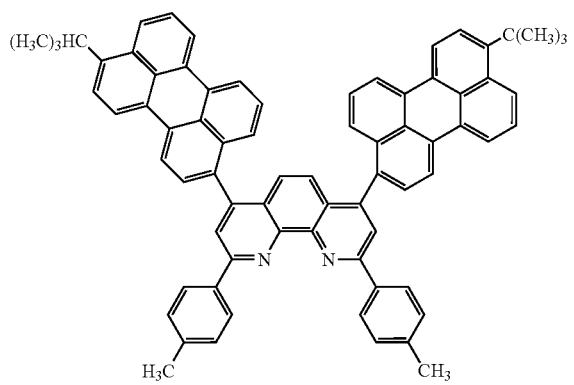
14
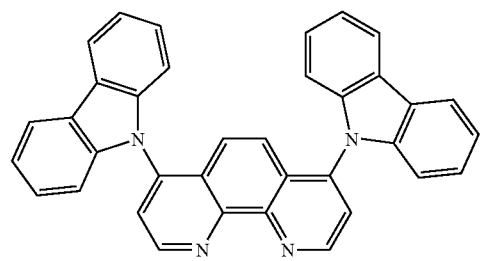
15
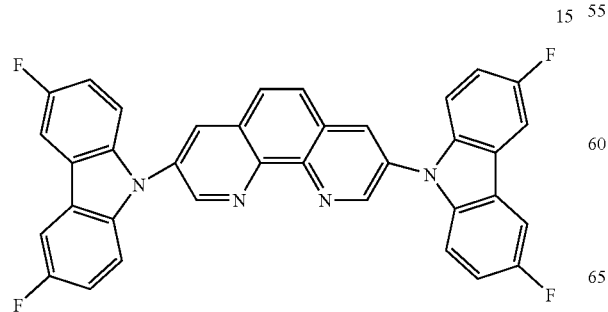
16
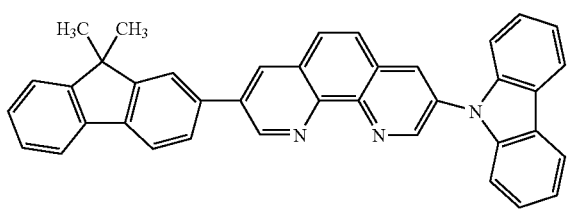
[II]
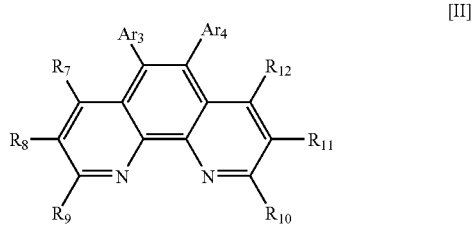
Typical Examples of Compounds of Formula [II]
Exemplary Compound Nos. 17-18
17
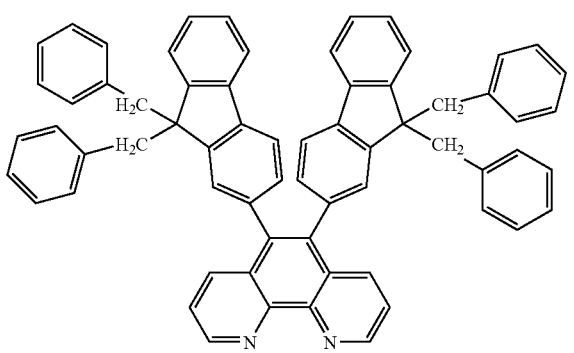
18
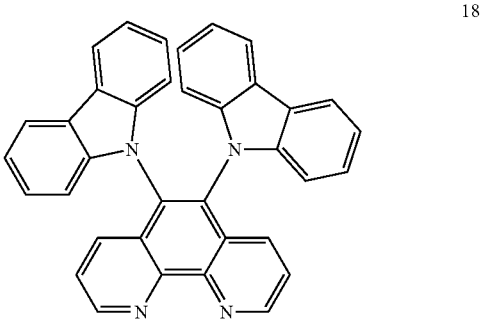
[III]
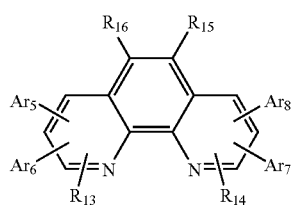

Typical Examples of Compounds of Formula [III]
Exemplary Compound Nos. 19-30
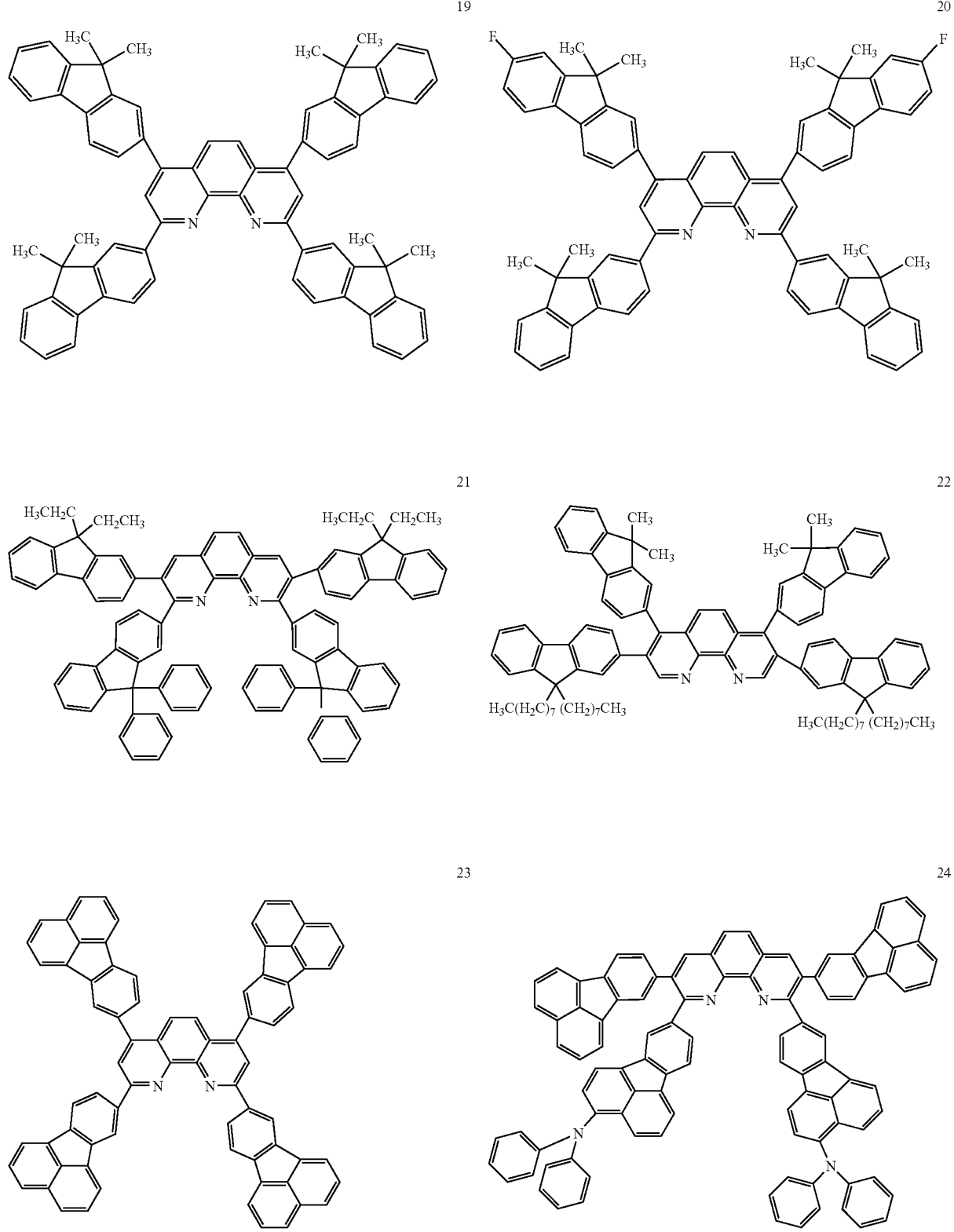

-continued
25
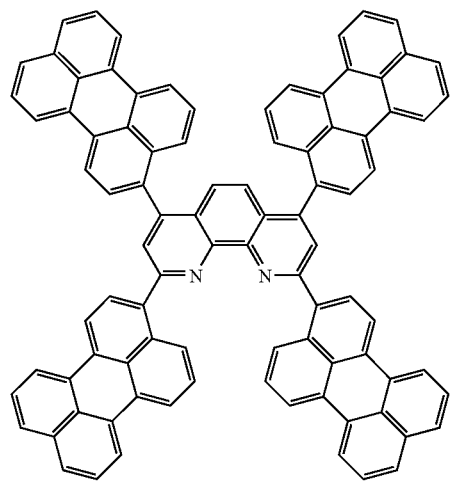
26
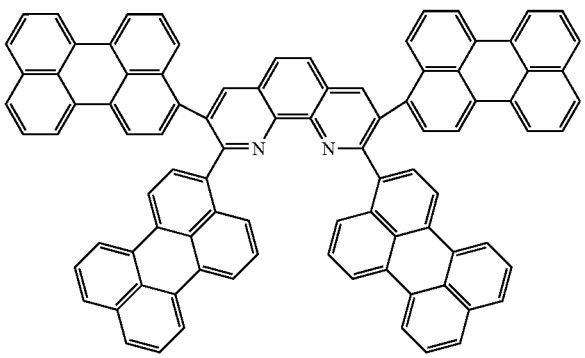
27
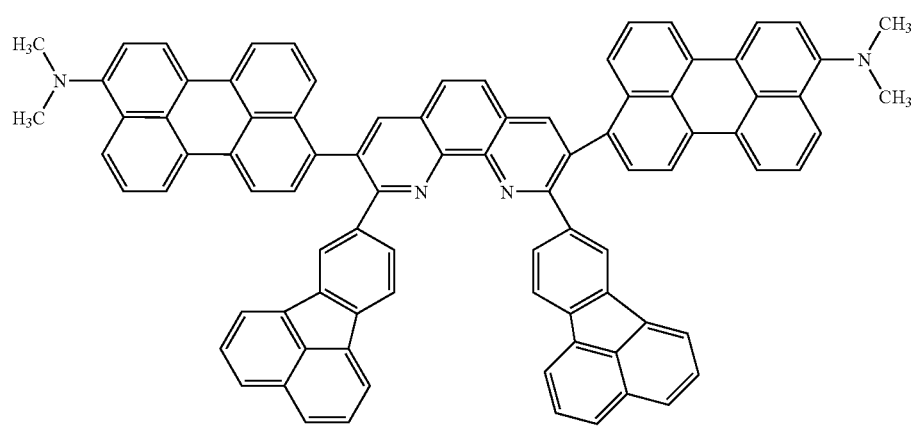
28
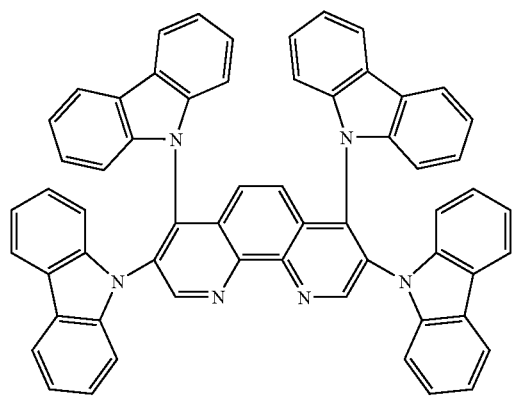
29
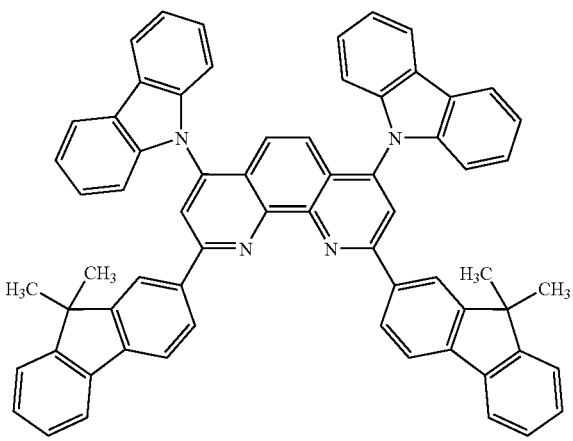

-continued

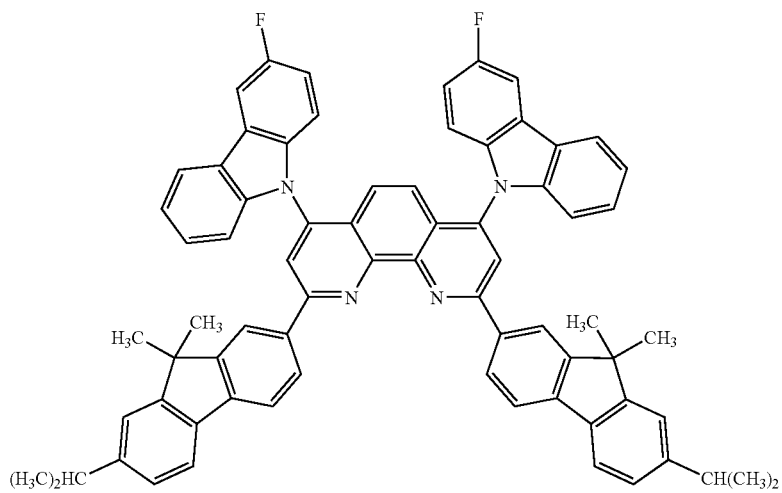

30

The phenanthroline compound of the present invention can be synthesized by generally known methods, in which it can be obtained by the synthesis such as the Suzuki coupling method using a palladium catalyst (e.g., Chem. Rev. 1995, 95, 2457-2483) through a phenanthroline compound intermediate that is obtained by the methods, for example, described in J. Org, Chem., 16, 941-945 (1951); Tetrahedron, Lett., 36, 3489-3490 (1995) and the like.

The phenanthroline compound of the present invention has superior electron transporting property and durability to the conventional compounds and is useful as a layer comprising an organic compound of an organic light emitting device, particularly as an electron transporting layer and a light emitting layer. Moreover, the layers formed by a vacuum evaporation process or a solution coating process are difficult to be crystallized and are excellent in long-term stability.

The organic light emitting device of the present invention will now be described in detail.

The organic light emitting device of the present invention comprises a pair of electrodes consisting of an anode and a cathode, and a layer comprising an organic compound comprising at least one of the phenanthroline compounds represented by the general formula [I], [II] and [III], interposed between the pair of electrodes.

In the organic light emitting device of the present invention, it is preferred that at least an electron transporting layer or a light emitting layer of the layer(s) comprised of an organic compound comprises at least one of the above-mentioned phenanthrolines.

In the organic light emitting device of the present invention, the phenanthroline compound represented by the above general formulas [I] to [III] is formed between the anode and the cathode by a vacuum evaporation process or a solution coating process. The organic layer is preferably formed in a thin film having a thickness of less than 10 μm, preferably 0.5 μm or less, more preferably from 0.01 to 0.5 μm.

FIGS. 1 to 6 are views illustrating preferred examples of the organic light emitting device of the present invention.

FIG. 1 is a sectional view illustrating one example of the organic light emitting device of the present invention. The device of FIG. 1 has the structure in which an anode 2, a light emitting layer 3 and a cathode 4 are provided on a substrate 1 in the mentioned order. The structure shown in FIG. 1 is useful when employing a compound having hole transportability, electron transportability and light emitting property singularly within itself, or when employing compounds having respective characteristics in mixture.

Figure 2:
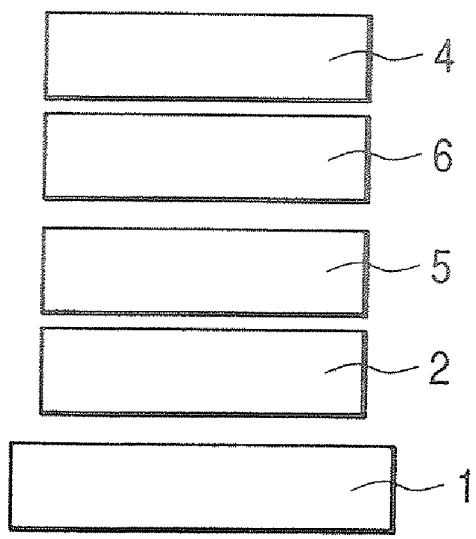
FIG. 2 is a sectional view illustrating another example of the organic light emitting device according to the present invention.

FIG. 2 is a sectional view illustrating another example of the organic light emitting device of the present invention. The device of FIG. 2 has the structure in which an anode 2, a hole transporting layer 5, an electron transporting layer 6 and a cathode 4 are provided on a substrate 1 in the mentioned order. The structure shown in FIG. 2 is useful when a material having a hole transportability and/or electron transportability is used for respective layers as a light emitting substance in combination with a hole transporting or electron transporting substance having no light emitting property. In this case, the light emitting layer comprises either the hole transporting layer 5 or the electron transporting layer 6.

Figure 3:
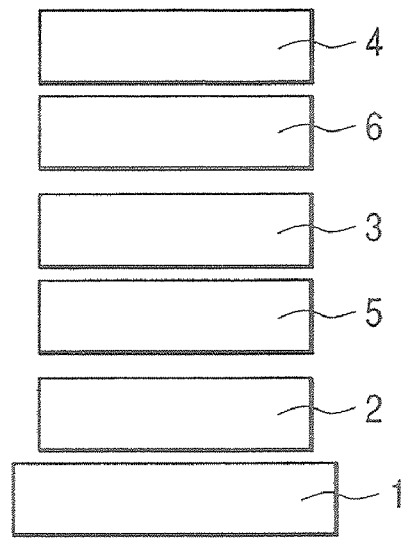
FIG. 3 is a sectional view illustrating still another example of the organic light emitting device according to the present invention.

FIG. 3 is a sectional view illustrating another example of the organic light emitting device of the present invention. The device of FIG. 3 has the structure in which an anode 2, a hole transporting layer 5, a light emitting layer 3, an electron transporting layer 6 and a cathode 4 are provided on a substrate 1 in the mentioned order. The structure is to separate a carrier transporting function and a light emitting function, and is used in suitable combination with compounds having the respective properties of hole transporting property, electron transporting property and light emitting property. Thus, the freedom of selection of materials is extremely increased, and various compounds having different emission wavelengths can be used to allow diversification of the luminescent hue. Further, carriers or excitons can be effectively confined in the central light emitting layer 3 to improve the light emission efficiency.

Figure 4:
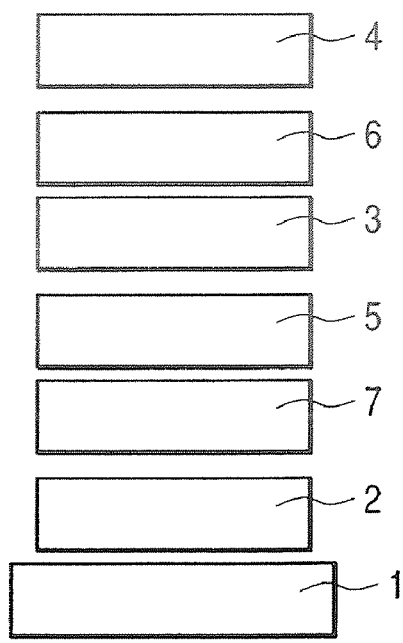
FIG. 4 is a sectional view illustrating yet another example of the organic light emitting device according to the present invention.

FIG. 4 is a sectional view illustrating another example of the organic light emitting device of the present invention. The device of FIG. 4 has the structure in which a hole injecting layer 7 is inserted to the anode 2 side as compared with the structure shown in FIG. 3. The structure shown in FIG. 1 is effective for improving adhesiveness of the anode 2 to the hole transporting layer 5 or improving the hole injecting property and is also effective for driving at a reduced voltage.

Figure 5:
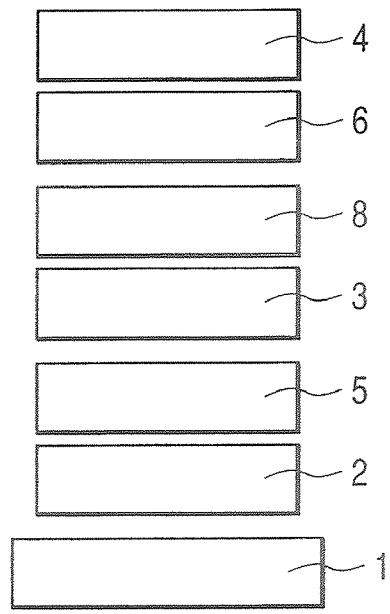
FIG. 5 is a sectional view illustrating yet still another example of the organic light emitting device according to the present invention.
Figure 6:
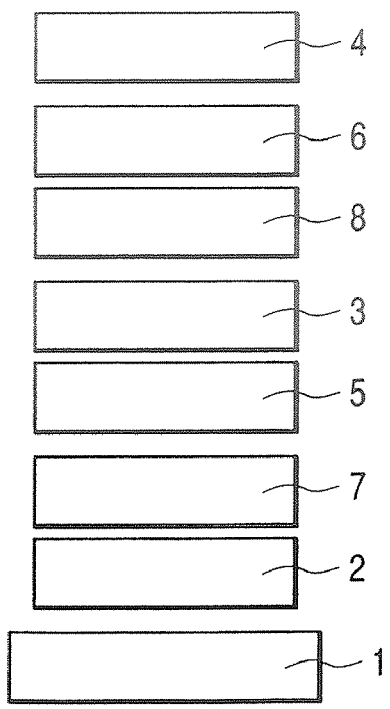
FIG. 6 is a sectional view illustrating yet again another example of the organic light emitting device according to the present invention.

FIGS. 5 and 6 are sectional views illustrating other examples of the organic light emitting device of the present invention. The devices of FIGS. 5 and 6 have the structures in which a layer (hole-blocking layer 8) for blocking holes or excitons from passing through to the cathode 4 side is inserted between the light emitting layer 3 and the electron transporting layer 6 as compared with FIGS. 3 and 4. The structure is effective for improving the light emission efficiency by using a compound having a very high ionization potential as the hole blocking layer 8.

It should be noted that FIGS. 1 to 6 merely show very basic device structures, and the structures of the organic light emitting device using the compounds of the present invention are not limited thereto. It is possible to take various structures, for example, to provide an insulating layer at an interface between an electrode and an organic layer, to provide an adhesion layer or an interference layer or to compose a hole transporting layer of two layers having different ionization potentials.

The phenanthroline compounds represented by the general formulas [I] to [III] used in the present invention are excellent in electron transporting property and durability compared with the conventional compounds, and can be used in any one of the structures shown in FIGS. 1 to 6.

Although the present invention uses the phenanthroline compounds represented by the general formulas [I] to [III] as constituent components for an electron transporting layer or a light emitting layer, already known hole transporting compounds, light emitting compounds or electron transporting compounds can also be used together as needed Examples of these compounds include the followings:

[Hole Transporting Compounds]

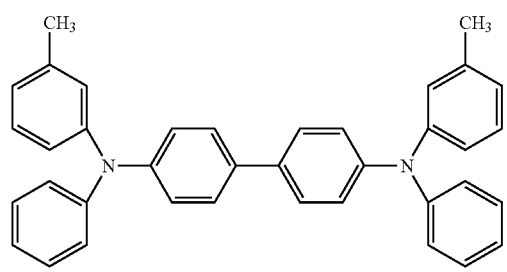

TPD

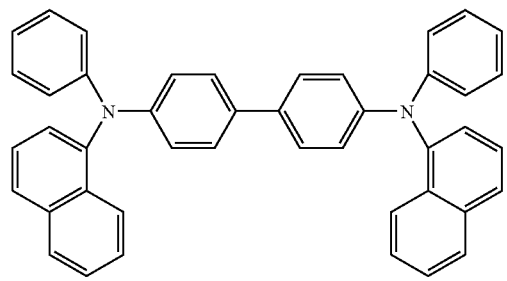

α-NPD

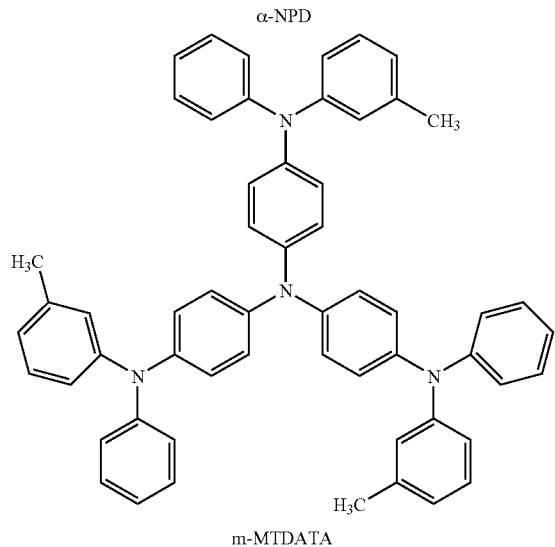

m-MTDATA

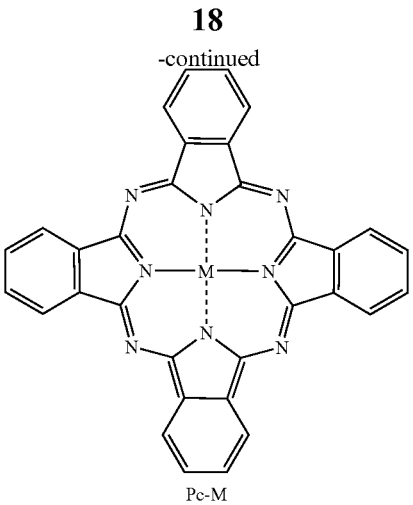

Pc-M
M: Cu, Mg, AlCl, TiO, SiCl$_2$, Zn, Sn, MnCl, GaCl, etc

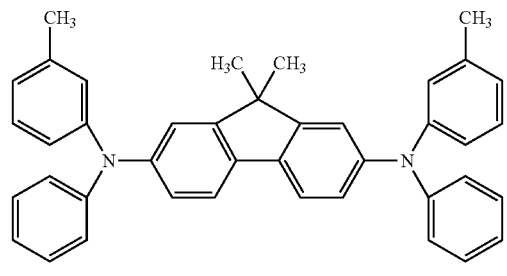

DTDPFL

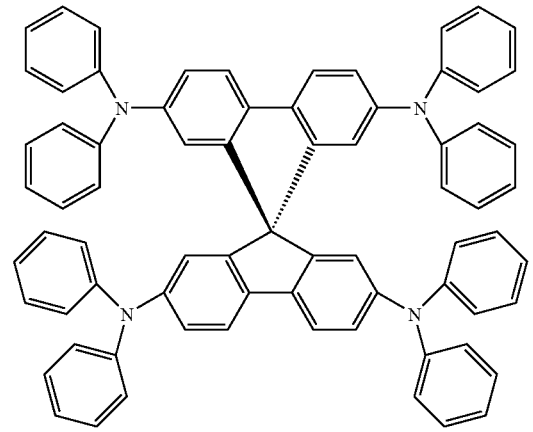

spiro-TPD

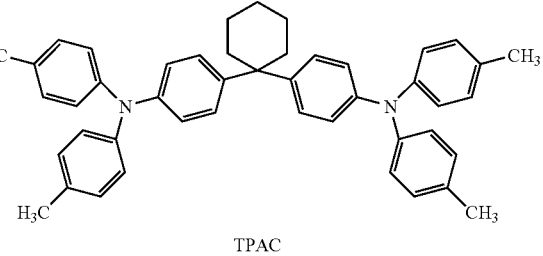

TPAC

-continued
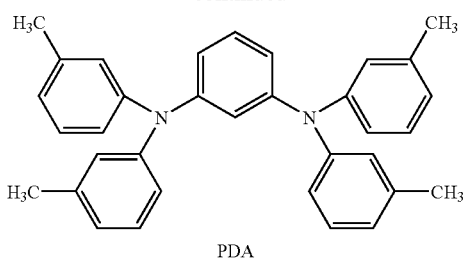
PDA
[Electron Transporting, Light Emitting Compounds]
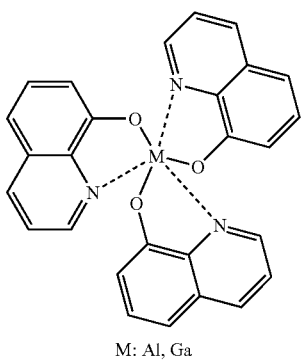
M: Al, Ga
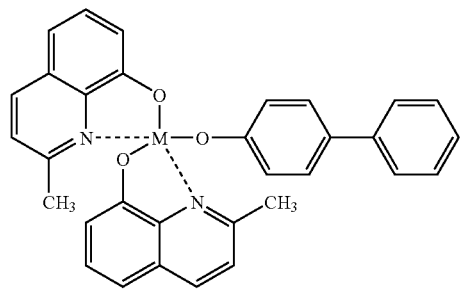
M: Al, Ga
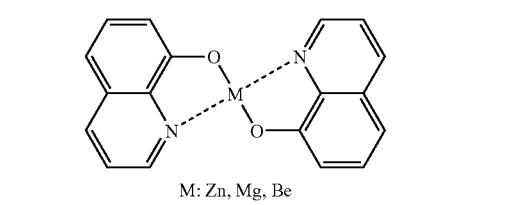
M: Zn, Mg, Be
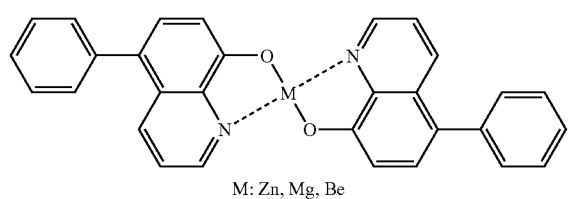
M: Zn, Mg, Be
-continued
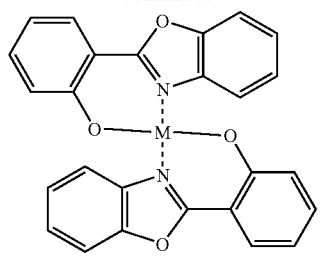
M: Zn, Mg, Be
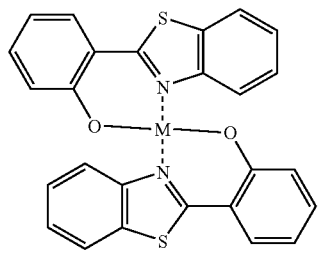
M: Zn, Mg, Be
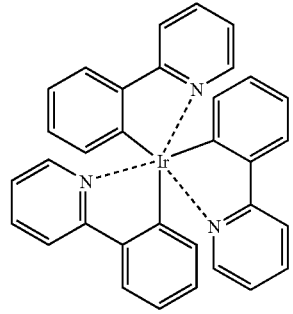
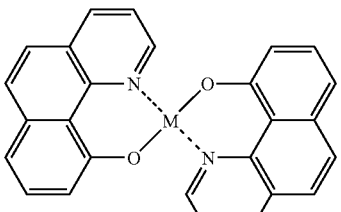
M: Zn, Mg, Be
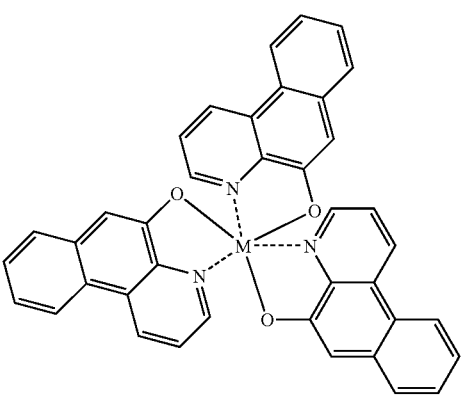
M: Al, Ga

[Light Emitting Compounds]
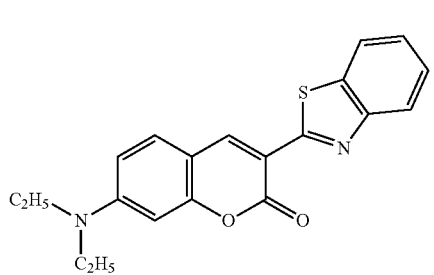
Coumarin 6
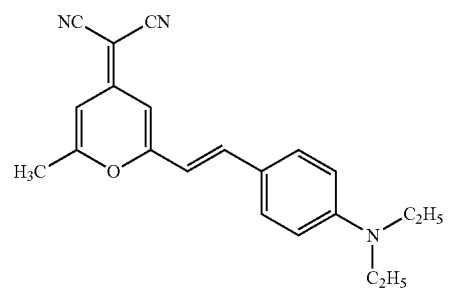
DCM-1
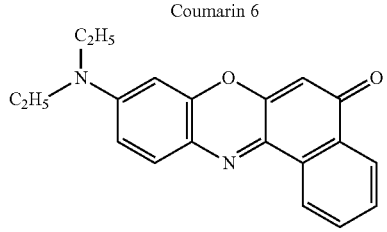
Nile red
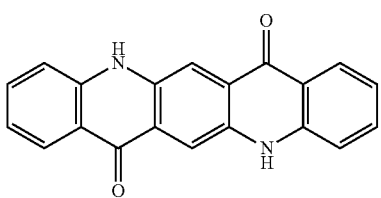
Quinacridone
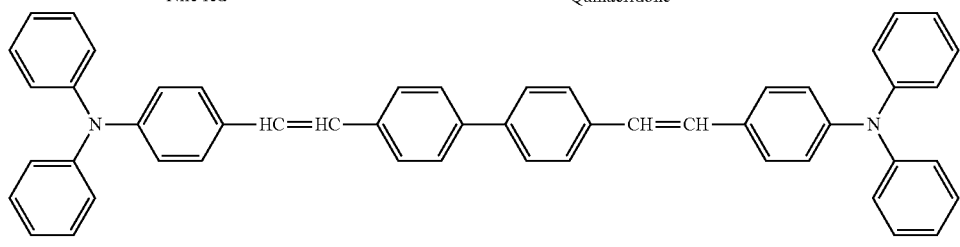
DTPABVi
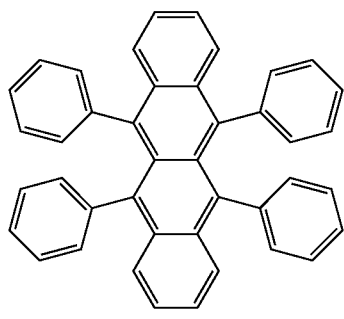
Rubrene
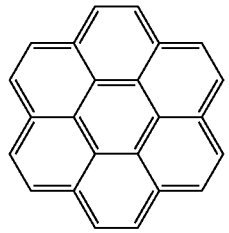
Coronene
[Light Emitting Layer Matrix Compounds/Electron Transporting Compounds]
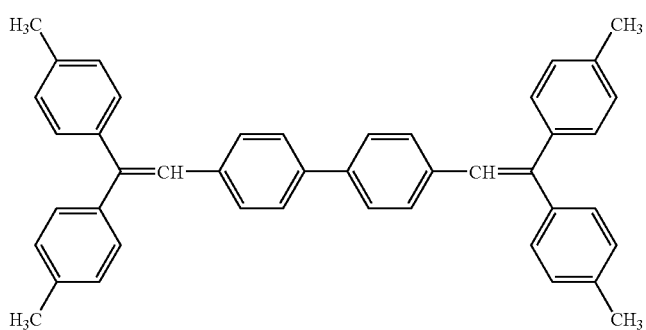

-continued
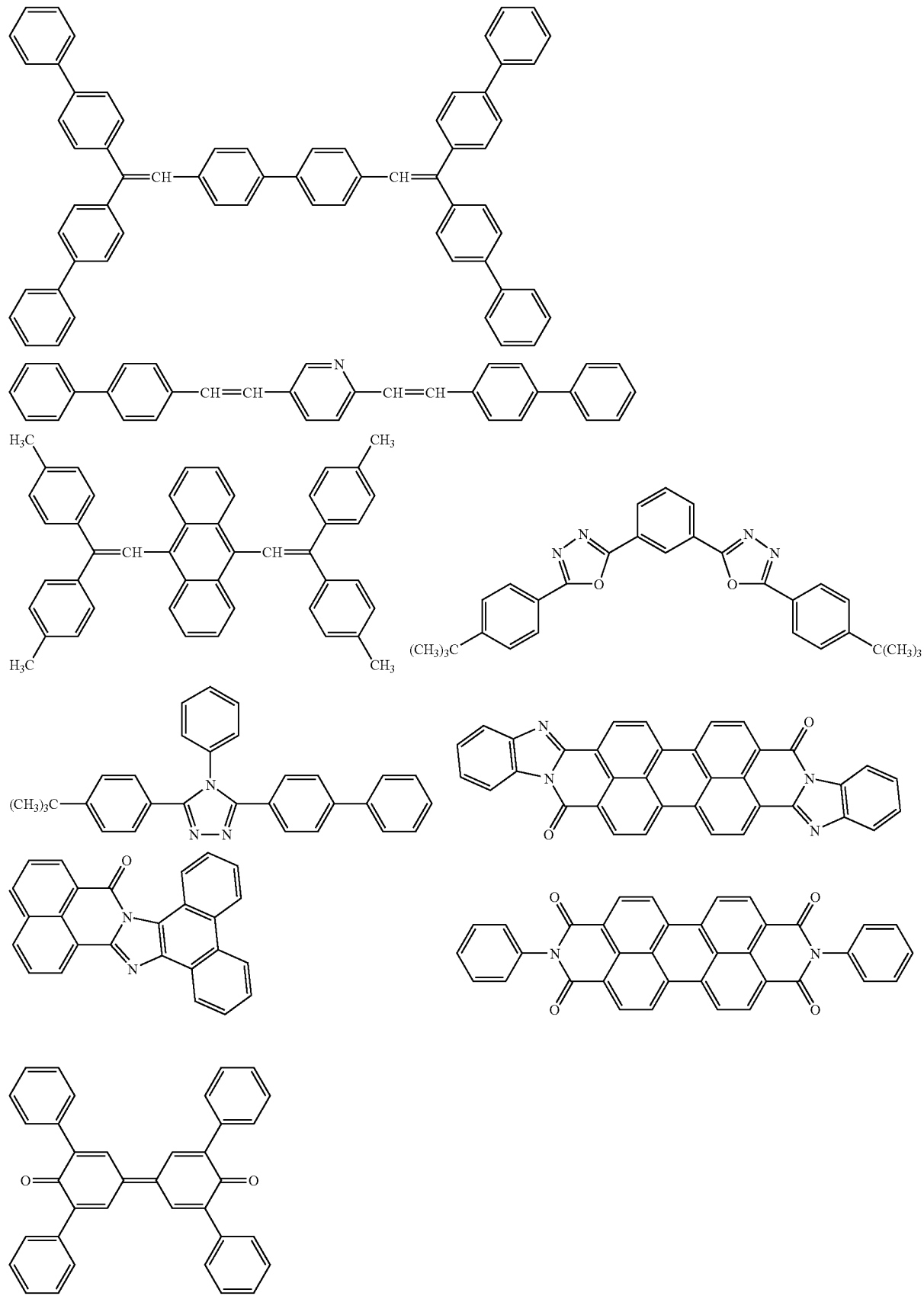

[Polymer-Based Hole Transporting Compounds]
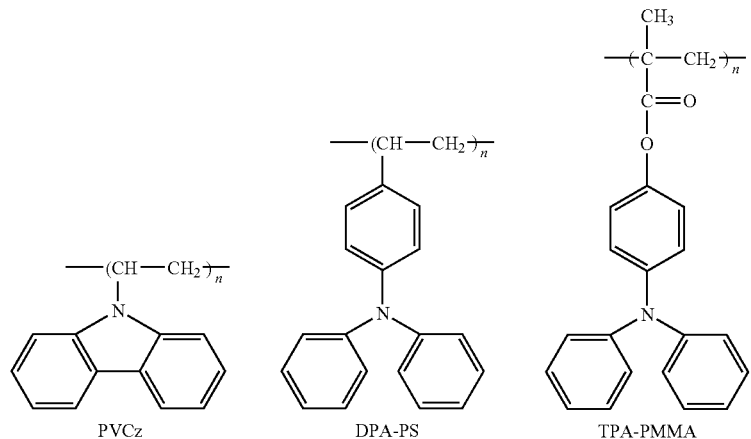
PVCz  DPA-PS  TPA-PMMA
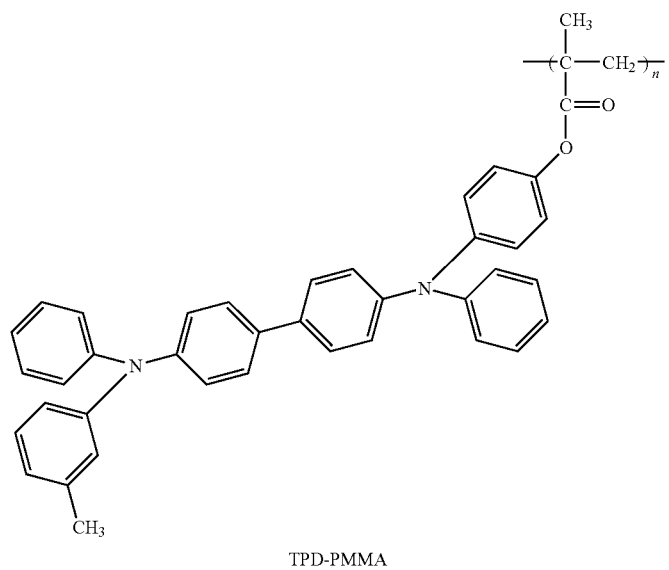
TPD-PMMA
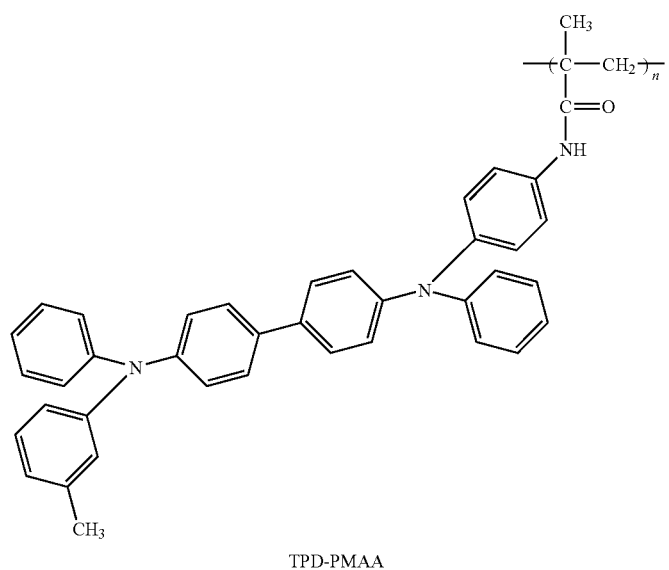
TPD-PMAA -continued

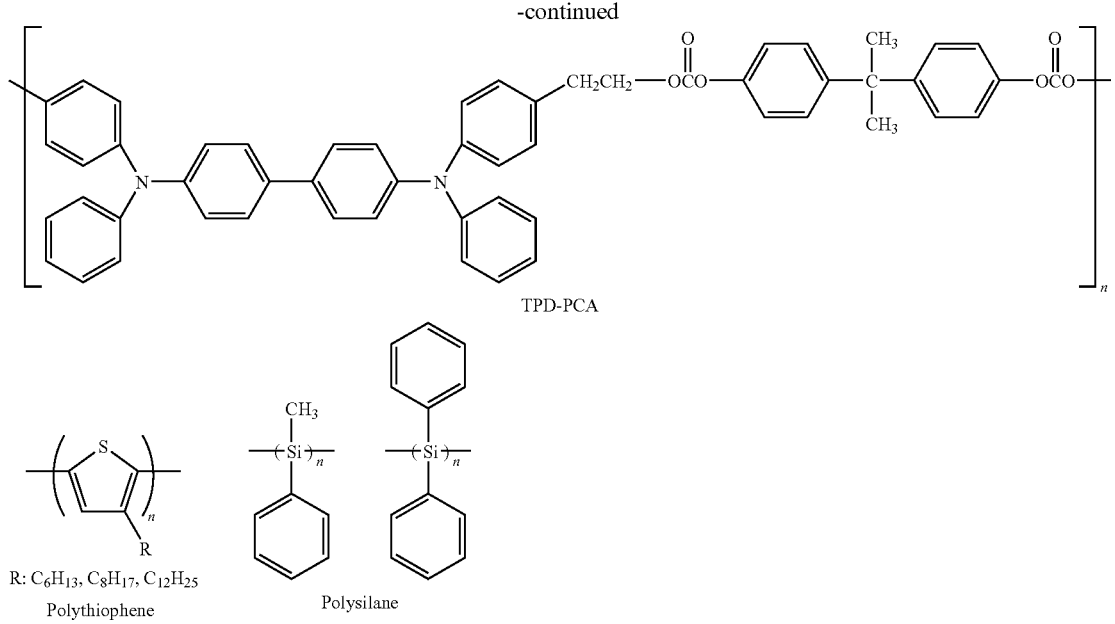
TPD-PCA

Polythiophene
R: $C_6H_{13}$, $C_8H_{17}$, $C_{12}H_{25}$

Polysilane

[Polymer-Based Light Emitting Compounds/Charge Transporting Compounds]

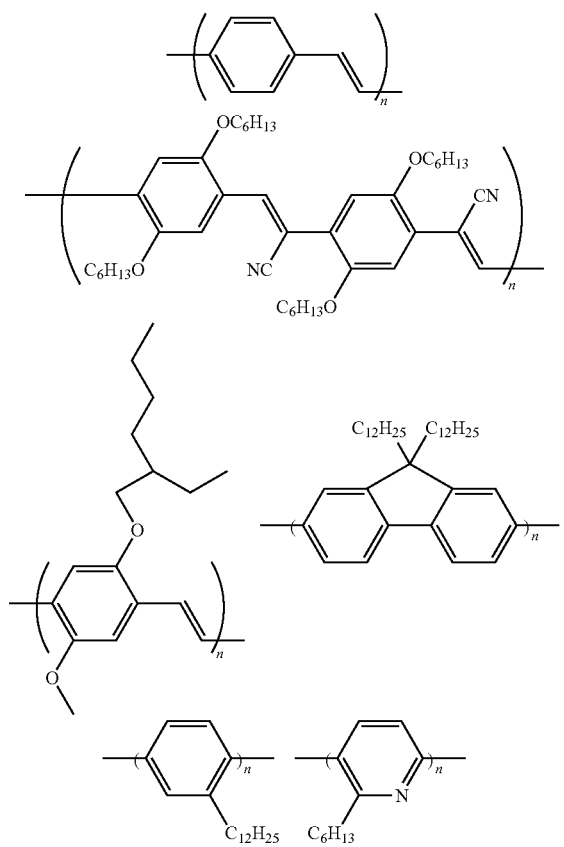

In the organic light emitting device of the present invention, the layers containing the phenanthroline compounds represented by the general formulas [I] to [III] and the layers containing other organic compounds are generally formed into thin films by a vacuum evaporation process or a coating process in which they are dissolved in a suitable solvent. In particular, when the film is formed by a coating process, it is also possible to form the film in combination with a suitable binder resin.

The binder resin can be selected from a wide range of binder resins, and include, for example, but not limited to, polyvinylcarbazole resins, polycarbonate resins, polyester resins, polyarylate resins, polystyrene resins, acrylic resins, methacrylic resins, butyral resins, polyvinylacetal resins, diallylphthalate resins, phenol resins, epoxy resins, silicone resins, polysulfone resins, urea resins and the like. In addition, one of them or a mixture of two or more of them may be used in the form of a homopolymer or a copolymer.

The materials for the anode preferably have a large work function, and metals such as, for example, gold, platinum, nickel, palladium, cobalt, selenium, vanadium and alloys thereof and metal oxides such as tin oxides, zinc oxides, indium tin oxides (ITO) and indium zinc oxides can be used. In addition, conductive polymers such as polyaniline, polypyrrole, polythiophene and polyphenylene sulfide can be used. These electrode materials can be used singularly or in combination.

On the other hand, the materials for the cathode preferably have a small work function, and metals such as lithium, sodium, potassium, cesium, calcium, magnesium, aluminium, indium, silver, lead, tin and chrome and alloys thereof can be used. Metal oxides such as indium tin oxides (ITO) can also be used. Moreover, the cathode may have either a one-layer structure or a multilayer structure.

The substrate for use in the present invention includes, but not limited to, metal substrates, opaque substrates such as ceramic substrates, and transparent substrates such as glass, quartz and plastic sheets. Moreover, it is possible to control the color of emitted light using a color filter film, a fluorescent color conversion filter film, a dielectric reflecting film and the like for the substrate.

Furthermore, a protective layer or an encapsulant layer can also be provided on the prepared device for the purpose of preventing contact with oxygen, moisture and the like. The

EXAMPLES

The present invention will now be described in detail with reference to examples, but the present invention is not limited to them.

Synthesis Example 1

Synthesis of Exemplary Compound No. 2

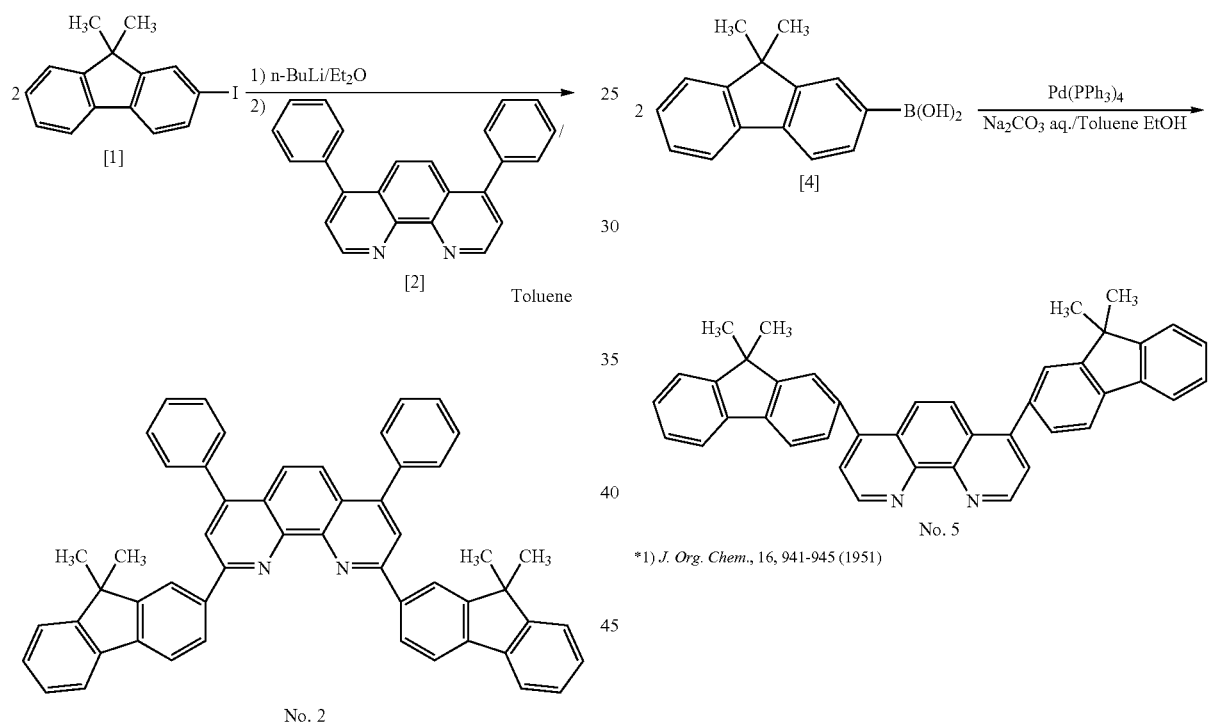

To a three-necked flask of 300 ml, 5.8 g (18.1 mmol) of 2-iodo-9,9-dimethylfluorene [1] and 80 ml of diethyl ether were charged and 11.7 ml (18.1 mmol) of n-butyllithium (hexane solution of 15%) was dropped under stirring at −78° C. in a nitrogen atmosphere. The mixture was raised to room temperature and stirred for one hour, and then cooled to −20° C. and a dispersion of 1.5 g (4.51 mmol) of bathophenanthroline [2] in 100 ml of toluene was dropped. The mixture was stirred at room temperature for 12 hours and was added with water. The organic layer was extracted with chloroform and dried with anhydrous sodium sulfate, and then purified with an alumina column (hexane/chloroform solvent mixture developer), obtaining 2.4 g (yield of 74%) of Exemplary Compound No. 2 (yellow crystal).

Synthesis Example 2

Synthesis of Exemplary Compound No. 5

*1) *J. Org. Chem.*, 16, 941-945 (1951)

To a three-necked flask of 500 ml, 1.0 g (2.96 mmol) of 4,7-dibromo-1,10-phenanthroline [3]*[1]), 2.8 g (11.8 mmol) of 9,9-dimethylfluorene-2-boronic acid [4], 140 ml of toluene and 70 ml of ethanol were charged and an aqueous solution of 12 g of sodium carbonate/60 ml of water was dropped under stirring at room temperature in a nitrogen atmosphere, and then 0.17 g (0.15 mmol) of tetrakis(triphenylphosphine)palladium (0) was added. After stirring at room temperature for 30 minutes, the mixture was raised to a temperature of 77° C. and stirred for 3 hours. After the reaction, the organic layer was extracted with chloroform and dried with anhydrous sodium sulfate, and then purified with an alumina column (hexane/chloroform solvent mixture developer), obtaining 1.5 g (yield of 90%) of Exemplary Compound No. 5 (white crystal).

Synthesis Example 3

Synthesis of Exemplary Compound No. 19

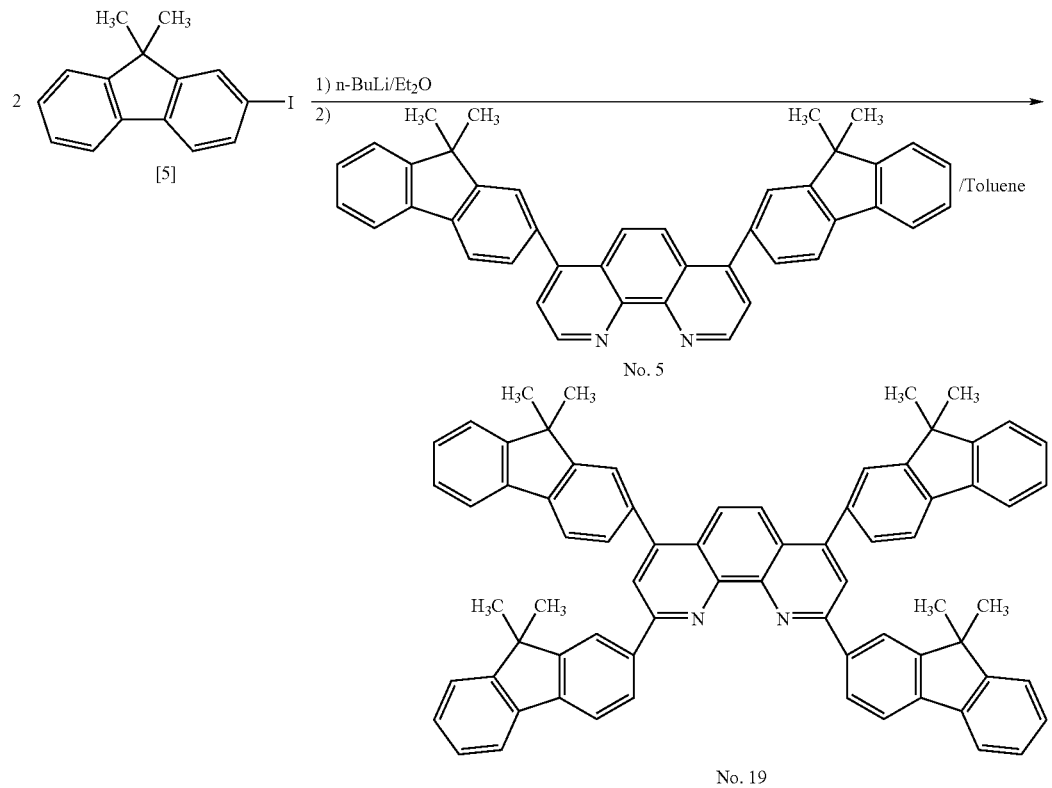

To a three-necked flask of 300 ml, 2.3 g (7.18 mmol) of 2-iodo-9,9-dimethylfluorene [5] and 60 ml of diethyl ether were charged and 4.6 ml (7.18 mmol) of n-butyllithium (hexane solution of 15%) was dropped under stirring at −78° C. in a nitrogen atmosphere. The mixture was raised to room temperature and stirred for one hour, and then cooled to −20° C. and a dispersion of 1.0 g (1.77 mmol) of Exemplary Compound No. 5 in 80 ml of toluene was dropped. The mixture was stirred at room temperature for 12 hours and was added with water. The organic layer was extracted with chloroform and dried with anhydrous sodium sulfate, and then purified with an alumina column (hexane/chloroform solvent mixture developer), obtaining 1.2 g (yield of 73%) of Exemplary Compound No. 19 (yellow crystal).

Synthesis Example 4

Synthesis of Exemplary Compound No. 8

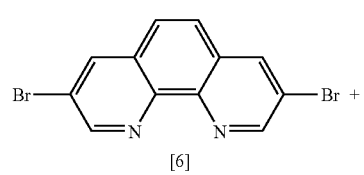

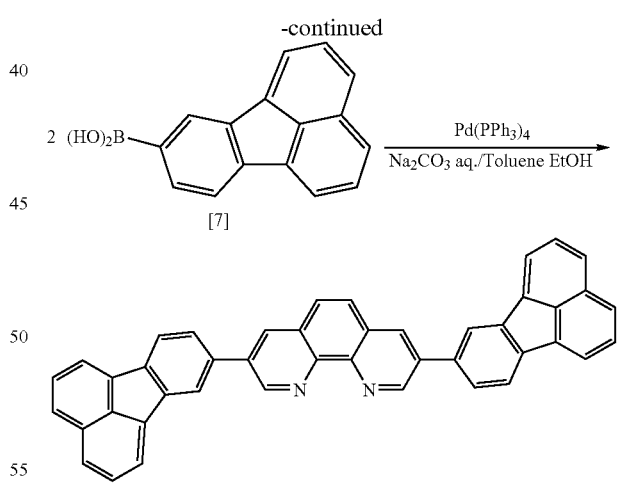

*2) *Tetrahedron, Lett.*, 36, 3489-3490 (1995)

To a three-necked flask of 500 ml, 1.0 g (2.96 mmol) of 3,8-dibromo-1,10-phenanthroline [6]*2), 2.9 g (11.8 mmol) of fluorantene-8-boronic acid [7], 140 ml of toluene and 70 ml of ethanol were charged and an aqueous solution of 12 g of sodium carbonate/60 ml of water was dropped under stirring at room temperature in a nitrogen atmosphere, and then 0.17 g (0.15 mmol) of tetrakis(triphenylphosphine)palladium (0) was added. After stirring at room temperature for 30 minutes, the mixture was raised to a temperature of 77° C. and stirred for 3 hours. After the reaction, the organic layer was extracted with chloroform and dried with anhydrous sodium sulfate, and then purified with an alumina column (hexane/chloroform solvent mixture developer), obtaining 1.4 g (yield of 82%) of Exemplary Compound No. 8 (yellow crystal).

Example 1

A device having the structure shown in FIG. 3 was prepared.

On a glass substrate as the substrate 1, indium tin oxide (ITO) as the anode 2 was deposited by a sputtering process in a thickness of 120 nm, the resultant structure being used as a transparent conductive supporting substrate. This was ultrasonically cleaned with acetone and isopropyl alcohol (IPA) in this order, and dried after the cleaning by boiling with IPA. Further, it was cleaned with UV/ozone. The resultant structure was used as a transparent conductive supporting substrate.

On the transparent conductive supporting substrate, a chloroform solution of the compound represented by the following structural formula was applied by a spin-coating process to form a film having a thickness of 30 nm, thus forming the hole transporting layer 5.

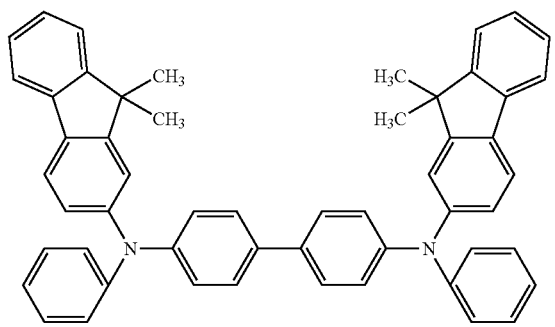

In addition, the Ir complex represented by the following structural formula and Exemplary Compound No. 1 as the instant phenanthroline compound (weight ratio of 5:100) were deposited by a vacuum evaporation process in a thickness of 20 nm to form the light emitting layer 3. As for the conditions, the degree of the vacuum at the evaporation was $1.0 \times 10^{-4}$ Pa and the film formation rate was 0.2-0.3 nm/sec.

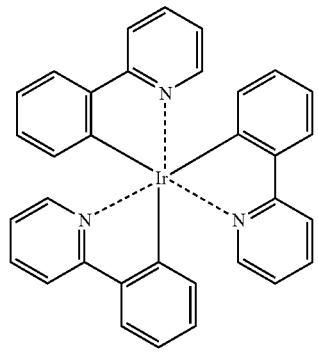

Moreover, trisquinolinol aluminium was deposited by a vacuum evaporation process in a thickness of 40 nm to form the electron transporting layer 6. As for the conditions, the degree of the vacuum at the evaporation was $1.0 \times 10^{-4}$ Pa and the film formation rate was 0.2-0.3 nm/sec.

Then, as the cathode 4, a vacuum evaporation material consisting of aluminium and lithium (lithium concentration of 1 atomic %) was used to form a metal layer film having a thickness of 50 nm on the above organic layer by a vacuum evaporation process, and further by the vacuum evaporation process an aluminium layer having a thickness of 150 nm was formed. As for the conditions, the degree of the vacuum at the evaporation was $1.0 \times 10^{-4}$ Pa and the film formation rate was 1.0-1.2 nm/sec.

Furthermore, the resultant structure was covered with a protective glass plate in a nitrogen atmosphere and sealed with an acrylic resin adhesive.

When the thus obtained device was applied with a DC voltage of 10 V using the ITO electrode (anode 2) as a positive electrode and the Al—Li electrode (cathode 4) as a negative electrode, the current passed through the device at a current density of 18.0 mA/cm$^2$ and emission of green light was observed at a luminance of 4,500 cd/m$^2$.

In addition, when the voltage was applied for 100 hours while maintaining the current density at 6.0 mA/cm$^2$, the initial luminance of 850 cd/m$^2$ dropped to 800 cd/m$^2$ after 100 hours, exhibiting only a small reduction of luminance.

Examples 2 to 9

Devices were prepared and evaluated in the same manner as in Example 1 with the exception that Exemplary Compounds shown in Table 1 below were used instead of Exemplary Compound No. 1. The results are shown in Table 1.

Comparative Examples 1 to 3

Devices were prepared and evaluated in the same manner as in Example 1 with the exception that Comparative Compound Nos. 1-3 shown below were used instead of Exemplary Compound No. 1. The results are shown in Table 1.

Comparative Compound No. 1

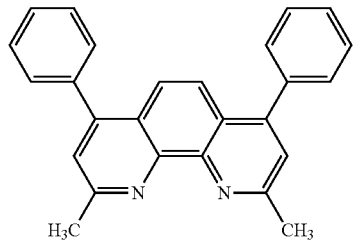

Comparative Compound No. 2

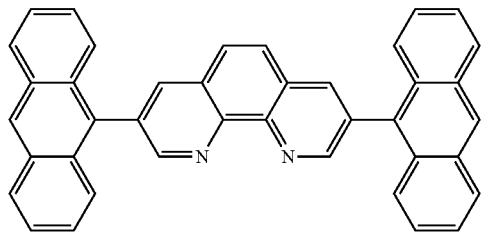

Comparative Compound No. 3

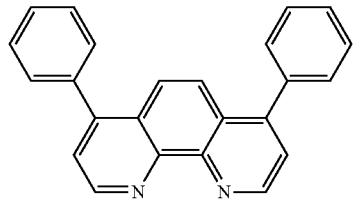

TABLE 1

| Example No. | Exemplary Compound No. | Initial | | Durability | | |
|---|---|---|---|---|---|---|
| | | Applied Voltage (V) | Luminance (cd/m$^2$) | Current Density (mA/cm$^2$) | Initial Luminance (cd/m$^2$) | Luminance after 100 hours (cd/m$^2$) |
| Example 1 | 1 | 10 | 4500 | 6.0 | 850 | 800 |
| Example 2 | 2 | 10 | 5000 | 6.0 | 1040 | 900 |
| Example 3 | 9 | 10 | 4300 | 6.0 | 760 | 680 |
| Example 4 | 11 | 10 | 4100 | 6.0 | 760 | 590 |
| Example 5 | 16 | 10 | 4320 | 6.0 | 800 | 590 |
| Example 6 | 19 | 10 | 4900 | 6.0 | 1000 | 750 |
| Example 7 | 22 | 10 | 4530 | 6.0 | 900 | 745 |
| Example 8 | 27 | 10 | 4400 | 6.0 | 830 | 670 |
| Example 9 | 30 | 10 | 4600 | 6.0 | 880 | 750 |
| Comparative Example 1 | Comparative Compound No. 1 | 10 | 760 | 6.0 | 430 | 200 |
| Comparative Example 2 | Comparative Compound No. 2 | 10 | 400 | 6.0 | 280 | 140 |
| Comparative Example 3 | Comparative Compound No. 3 | 10 | 1200 | 6.0 | 730 | 300 |

Example 10

A device of the structure shown in FIG. 3 was prepared.

The hole transporting layer 5 was formed on the transparent conductive supporting substrate in the same manner as in Example 1.

In addition, coumarin and trisquinolinol aluminium (polymerization ratio of 1:20) were deposited by a vacuum evaporation process in a thickness of 20 nm to form the light emitting layer 3. As for the conditions, the degree of the vacuum at the evaporation was 1.0×10$^{-4}$ Pa and the film formation rate was 0.2-0.3 nm/sec.

Moreover, Exemplary Compound No. 3 was deposited in a thickness of 40 nm to form the electron transporting layer 6. As for the conditions, the degree of the vacuum at the evaporation was 1.0×10$^{-4}$ Pa and the film formation rate was 0.2-0.3 nm/sec.

Then, the device was sealed after the cathode 4 was formed in the same manner as in Example 1.

When the thus obtained device was applied with a DC voltage of 8 V using the ITO electrode (anode 2) as a positive electrode and the Al—Li electrode (cathode 4) as a negative electrode, the current passed through the device at a current density of 1,110 mA/cm$^2$ and emission of green light was observed at a luminance of 95,000 cd/m$^2$.

Furthermore, when the voltage was applied for 100 hours while maintaining the current density at 200 mA/cm$^2$, the initial luminance of 10,000 cd/m$^2$ dropped to 8,500 cd/m$^2$ after 100 hours, exhibiting only a small reduction of luminance.

Examples 11 to 18

Devices were prepared and evaluated in the same manner as in Example 10 with the exception that Exemplary Compounds shown in Table 2 were used instead of Exemplary Compound No. 3. The results are shown in Table 2.

Comparative Examples 4 to 6

Devices were prepared and evaluated in the same manner as in Example 10 with the exception that Comparative Compound Nos. 1 to 3 were used instead of Exemplary Compound No. 3. The results are shown in Table 2.

TABLE 2

| Example No. | Exemplary Compound No. | Initial | | Durability | | |
|---|---|---|---|---|---|---|
| | | Applied Voltage (V) | Luminance (cd/m$^2$) | Current Density (mA/cm$^2$) | Initial Luminance (cd/m$^2$) | Luminance after 100 hours (cd/m$^2$) |
| Example 10 | 3 | 8 | 95000 | 200 | 10000 | 8500 |
| Example 11 | 1 | 8 | 96000 | 200 | 14000 | 8750 |
| Example 12 | 8 | 8 | 83000 | 200 | 13800 | 8680 |
| Example 13 | 10 | 8 | 80000 | 200 | 13050 | 8700 |
| Example 14 | 15 | 8 | 96000 | 200 | 13000 | 8540 |
| Example 15 | 21 | 8 | 98000 | 200 | 15000 | 9750 |
| Example 16 | 23 | 8 | 79000 | 200 | 11500 | 8600 |
| Example 17 | 26 | 8 | 78000 | 200 | 11000 | 8560 |
| Example 18 | 28 | 8 | 84000 | 200 | 13000 | 8800 |
| Comparative Example 4 | Comparative Compound No. 1 | 8 | 14000 | 200 | 7000 | 3500 |
| Comparative Example 5 | Comparative Compound No. 2 | 8 | 15000 | 200 | 6000 | 2800 |
| Comparative Example 6 | Comparative Compound No. 3 | 8 | 15600 | 200 | 8000 | 4000 |

Example 19

A device with the structure shown in FIG. 3 was prepared.

The hole transporting layer 5 was formed on the transparent conductive supporting substrate in the same manner as in Example 1.

In addition, the Ir complex represented by the following structural formula and the carbazole compound represented by the following structural formula (polymerization ratio of 5:100) were deposited by a vacuum evaporation process in a thickness of 20 nm to form the light emitting layer 3. As for the conditions, the degree of the vacuum at the evaporation was $1.0 \times 10^{-4}$ Pa and the film formation rate was 0.2-0.3 nm/sec.

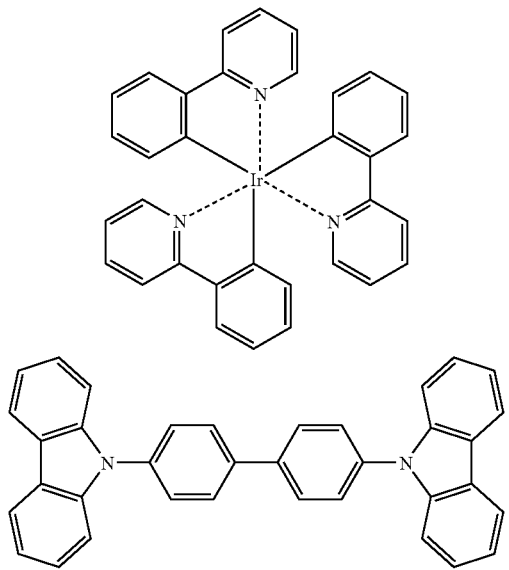

Moreover, Exemplary Compound No. 5 was deposited in a thickness of 40 nm to form the electron transporting layer 6. As for the conditions, the degree of the vacuum at the evaporation was $1.0 \times 10^{-4}$ Pa and the film formation rate was 0.2-0.3 nm/sec.

The device was then sealed after the cathode 4 was formed in the same manner as in Example 1.

When the thus obtained device was applied with a DC voltage of 10 V using the ITO electrode (anode 2) as a positive electrode and the Al—Li electrode (cathode 4) as a negative electrode, the current passed through the device at a current density of 20.0 mA/cm$^2$ and emission of green light was observed at a luminance of 6,800 cd/m$^2$.

Furthermore, when the voltage was applied for 100 hours while maintaining the current density at 60 mA/cm$^2$ the initial luminance of 1,300 cd/m$^2$ dropped to 1,150 cd/m$^2$ after 100 hours, exhibiting only a small reduction of luminance.

Examples 20 to 31

Devices were prepared and evaluated in the same manner as in Example 19 with the exception that Exemplary Compounds shown in Table 3 were used instead of Exemplary Compound No. 5. The results are shown in Table 3.

Comparative Examples 7 to 9

Devices were prepared and evaluated in the same manner as in Example 19 with the exception that Comparative Compound Nos. 1 to 3 were used instead of Exemplary Compound No. 5. The results are shown in Table 3.

TABLE 3

| | | Initial | | Durability | | |
|---|---|---|---|---|---|---|
| Example No. | Exemplary Compound No. | Applied Voltage (v) | Luminance (cd/m$^2$) | Current Density (mA/cm$^2$) | Initial Luminance (cd/m$^2$) | Luminance after 100 hours (cd/m$^2$) |
| Example 19 | 5 | 10 | 6800 | 6.0 | 1300 | 1150 |
| Example 20 | 4 | 10 | 5400 | 6.0 | 950 | 700 |
| Example 21 | 6 | 10 | 6750 | 6.0 | 1298 | 1130 |
| Example 22 | 7 | 10 | 6580 | 6.0 | 1050 | 880 |
| Example 23 | 12 | 10 | 6510 | 6.0 | 1040 | 800 |
| Example 24 | 13 | 10 | 6410 | 6.0 | 1056 | 800 |
| Example 25 | 14 | 10 | 6680 | 6.0 | 1110 | 900 |
| Example 26 | 18 | 10 | 5800 | 6.0 | 903 | 690 |
| Example 27 | 19 | 10 | 5600 | 6.0 | 960 | 700 |
| Example 28 | 20 | 10 | 6730 | 6.0 | 1220 | 980 |
| Example 29 | 24 | 10 | 5800 | 6.0 | 960 | 700 |
| Example 30 | 25 | 10 | 5980 | 6.0 | 970 | 610 |
| Example 31 | 28 | 10 | 6680 | 6.0 | 990 | 710 |
| Comparative Example 7 | Comparative Compound No. 1 | 10 | 840 | 6.0 | 500 | 230 |
| Comparative Example 8 | Comparative Compound No. 2 | 10 | 500 | 6.0 | 300 | 150 |
| Comparative Example 9 | Comparative Compound No. 3 | 10 | 1300 | 6.0 | 800 | 300 |

As described above by illustrating embodiments and examples, the organic light emitting devices using the phenanthroline compounds represented by the general formulas [I] to [III] provide the emission having a high luminance at a low applied voltage and are also excellent in durability Particularly, the organic layers comprising the phenanthroline compounds of the present invention are excellent as an electron transporting layer as well as a light emitting layer.

Moreover, it is possible to prepare the devices by using a vacuum evaporation process, casting process or the like, and the devices having a large area can be prepared easily at a relatively low cost.

The invention claimed is:

1. An organic light emitting device comprising:
   an anode and a cathode; and
   an organic compound layer interposed between the anode and the cathode and comprising a light emitting layer and an electron transporting layer,
   wherein at least one of the light emitting layer and the electron transporting layer comprises a phenanthroline compound represented by the general formula [I]:

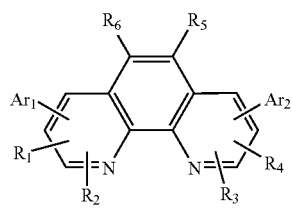

wherein $R_1$, $R_2$, $R_3$, $R_4$, $R_5$, and $R_6$ are each a hydrogen atom, and $Ar_1$ and $Ar_2$ are the same or different and are each a fluorenyl group represented by the general formula [IV]:

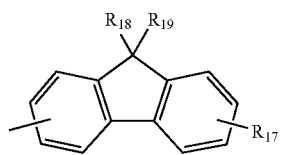

wherein $R_{17}$ is a hydrogen atom, and $R_{18}$ and $R_{19}$ are the same or different and are each selected from a hydrogen atom, a methyl group, an ethyl group, an n-propyl group, an isopropyl group, an n-butyl group, a tert-butyl group, and an octyl group.

2. The organic light emitting device according to claim 1, wherein the phenanthroline compound is represented by the structural formula:

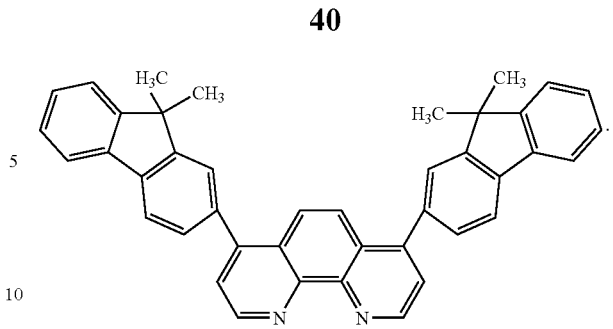

3. The organic light emitting device according to claim 1, wherein the phenanthroline compound is represented by the structural formula:

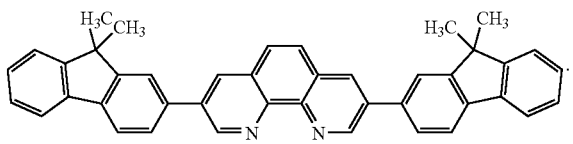

4. The organic light emitting device according to claim 1, wherein the phenanthroline compound is represented by the structural formula:

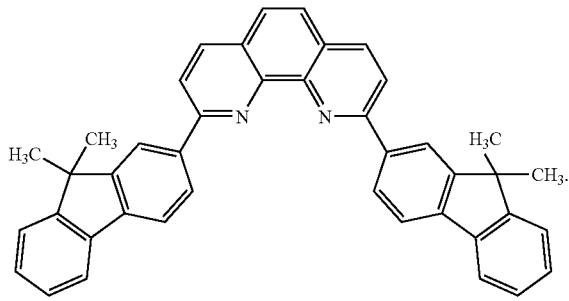

5. The organic light emitting device according to claim 1, wherein the light emitting layer comprises the phenanthroline compound.

6. The organic light emitting device according to claim 1, wherein the electron transporting layer comprises the phenanthroline compound.

7. The organic light emitting device according to claim 1, which emits green light.

* * * * *